US007800366B1

United States Patent
Prince et al.

(10) Patent No.: US 7,800,366 B1
(45) Date of Patent: Sep. 21, 2010

(54) THREE DIMENSIONAL MAGNETIC RESONANCE MOTION ESTIMATION ON A SINGLE IMAGE PLANE

(75) Inventors: Jerry L. Prince, Lutherville, MD (US); Matthias Stuber, Elliott City, MD (US); Nael Fakhry Osman, Baltimore, MD (US); Khaled Zakarya Abd-Elmoniem, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 40 days.

(21) Appl. No.: 12/353,215

(22) Filed: Jan. 13, 2009

Related U.S. Application Data

(63) Continuation of application No. 11/418,563, filed on May 4, 2006, now Pat. No. 7,495,438.

(60) Provisional application No. 60/677,770, filed on May 4, 2005.

(51) Int. Cl.
*G01V 3/00* (2006.01)
(52) U.S. Cl. .................................... 324/307
(58) Field of Classification Search ......... 324/300–322; 600/407–445
See application file for complete search history.

(56) References Cited

U.S. PATENT DOCUMENTS 5,111,820 A * 5/1992 Axel et al. .................. 600/413
5,275,163 A * 1/1994 McKinnon et al. .......... 600/413
6,453,187 B1 * 9/2002 Prince et al. ................ 600/410
6,597,935 B2 * 7/2003 Prince et al. ................ 600/410
6,694,166 B2 * 2/2004 Salome et al. .............. 600/410
6,892,089 B1 * 5/2005 Prince et al. ................ 600/410
7,495,438 B2 * 2/2009 Prince et al. ................ 324/309
7,620,444 B2 * 11/2009 Le et al. ..................... 600/428
2009/0175562 A1 * 7/2009 Pan et al. .................... 382/312

* cited by examiner

*Primary Examiner*—Brij B Shrivastav
(74) *Attorney, Agent, or Firm*—Fernandez & Associates, LLP

(57) ABSTRACT

Three-dimensional MR motion estimation on a single image plane based on tagged MRI and HARP processing. Tagged magnetic resonance imaging technique encodes and automatically tracks displacement of spatially modulated object in three dimensions, encoding both in plane and through-plane motion in a single image plane without affecting acquisition speed. Post-processing unravels encoding in order to directly track 3-D displacement of points within the image plane throughout image sequence. The invention is particularly suited to use on a heart for tracking and determining myocardial displacement. In one embodiment, an MR pulse sequence extends a slice following complementary spatial modulation of magnetization (CSPAMM) pulse sequence with two small z-encoding gradients immediately before the readouts in successive CSPAMM acquisitions, thereby adding a through-plane encoding from which through-plane motion can be computed from acquired images. HARP processing is used to determine in-plane motion, after which through-plane position can be determined using phase encodings. Use of balanced encodings and horizontal and vertical tags permits cancellation of systematic phase artifacts present in CSPAMM acquisitions.

14 Claims, 19 Drawing Sheets

(a)
Human equatorial SA slice. Strain Comparison. Through-plane rotation adds false negative strain
(a) Segments: 1,2: Septal, 3,4: Interior, 5,6: Lateral, 7,8: Inferior.

(b) Circumferential strain ($E_{CC}$) before correction (green) and after correction (red).
True $E_{CC}$ (compression) is less than the apparent

Fig. 2-a (1-b) Horizontal Tag Acquisition with Negative z-encode $$I_h \propto \rho e^{j\varphi_e} \cos(\omega y - \varphi_y) e^{-j\varphi_z}$$

$$= \rho \frac{e^{j(\varphi_e - \varphi_z + \varphi_y - \omega y)} + e^{j(\varphi_e - \varphi_z - \varphi_y + \omega y)}}{2}$$

(2) Fourier Transform $$\mathcal{F}\left\{\rho e^{j(\varphi_e - \varphi_z - \varphi_y)}\right\} * \delta\left(k_y - \frac{\omega}{2\pi}\right) +$$
$$\mathcal{F}\left\{\rho e^{j(\varphi_e - \varphi_z + \varphi_y)}\right\} * \delta\left(k_y + \frac{\omega}{2\pi}\right)$$

(3) Harmonic Peak Demodulation & Filtering $$\mathcal{F}\left\{\rho e^{j(\varphi_e - \varphi_z + \varphi_y)}\right\} * \delta(k_y)$$

$$\mathcal{F}\left\{\rho e^{j(\varphi_e - \varphi_z - \varphi_y)}\right\} * \delta(k_y)$$

(4) Inverse Fourier Transform $\mathcal{F}^{-1}$ $$\rho e^{j(\varphi_e - \varphi_z - \varphi_y)} \qquad \rho e^{j(\varphi_e - \varphi_z + \varphi_y)}$$

(5) Phase Image Extraction $$\phi_C = \varphi_e - \varphi_z - \varphi_y \qquad \phi_D = \varphi_e - \varphi_z + \varphi_y$$

Fig. 2-b $I_v$  $I_h$ 
$\phi_A = \varphi_e + \varphi_z - \varphi_x$  $\phi_B = \varphi_e + \varphi_z + \varphi_x$ 
$\phi_C = \varphi_e - \varphi_z - \varphi_y$ 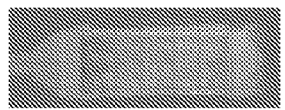 $\phi_D = \varphi_e - \varphi_z + \varphi_y$ 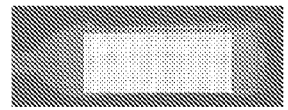
$\varphi x$ 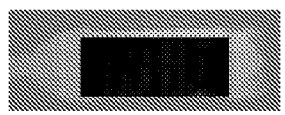 $\varphi y$ 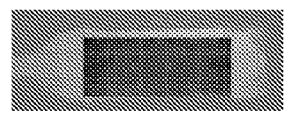
$\varphi_z$ using zHARP  $\varphi_z$ using PC 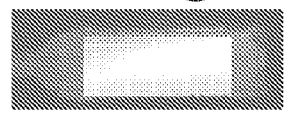
Fig. 4

Phantom in-plane and through-plane displacements

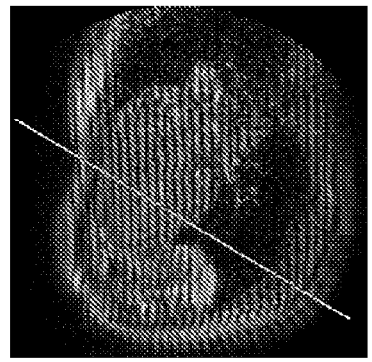
(a)
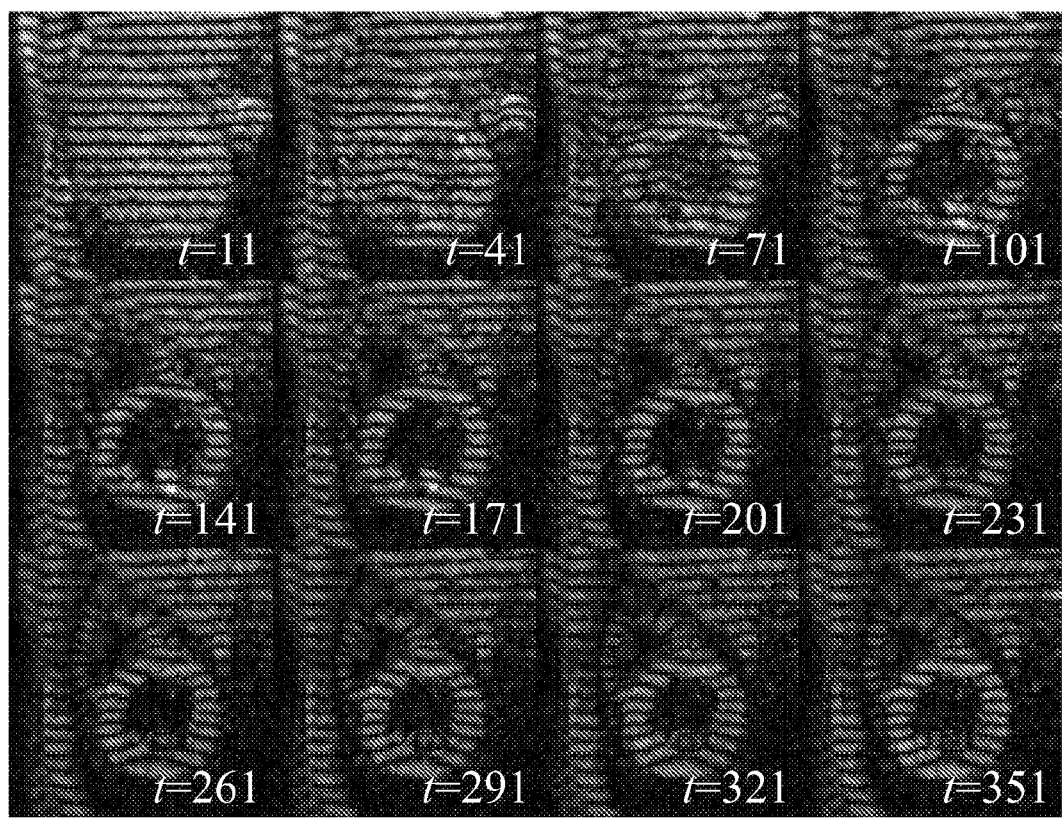
(b)
Fig. 10

False apparent strain due to through-plane rotation $\varphi$.

Strain before and after correction.
(Green) Through-plane rotation not corrected. False strain of ~2% is apparent.
(Red) Using $u_z$ to remove the effect of the through-plane rotation.

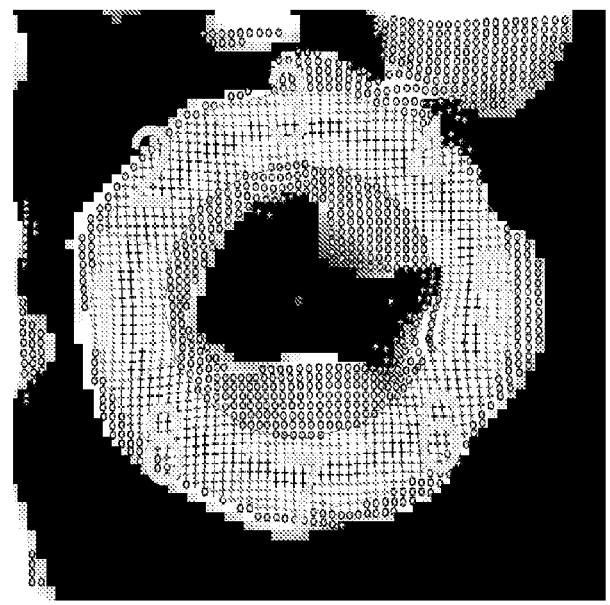
(a)
Human equatorial SA slice. Strain Comparison. Through-plane rotation adds false negative strain
(a) Segments: 1,2: Septal, 3,4: Interior, 5,6: Lateral, 7,8: Inferior.
Fig. 16-a

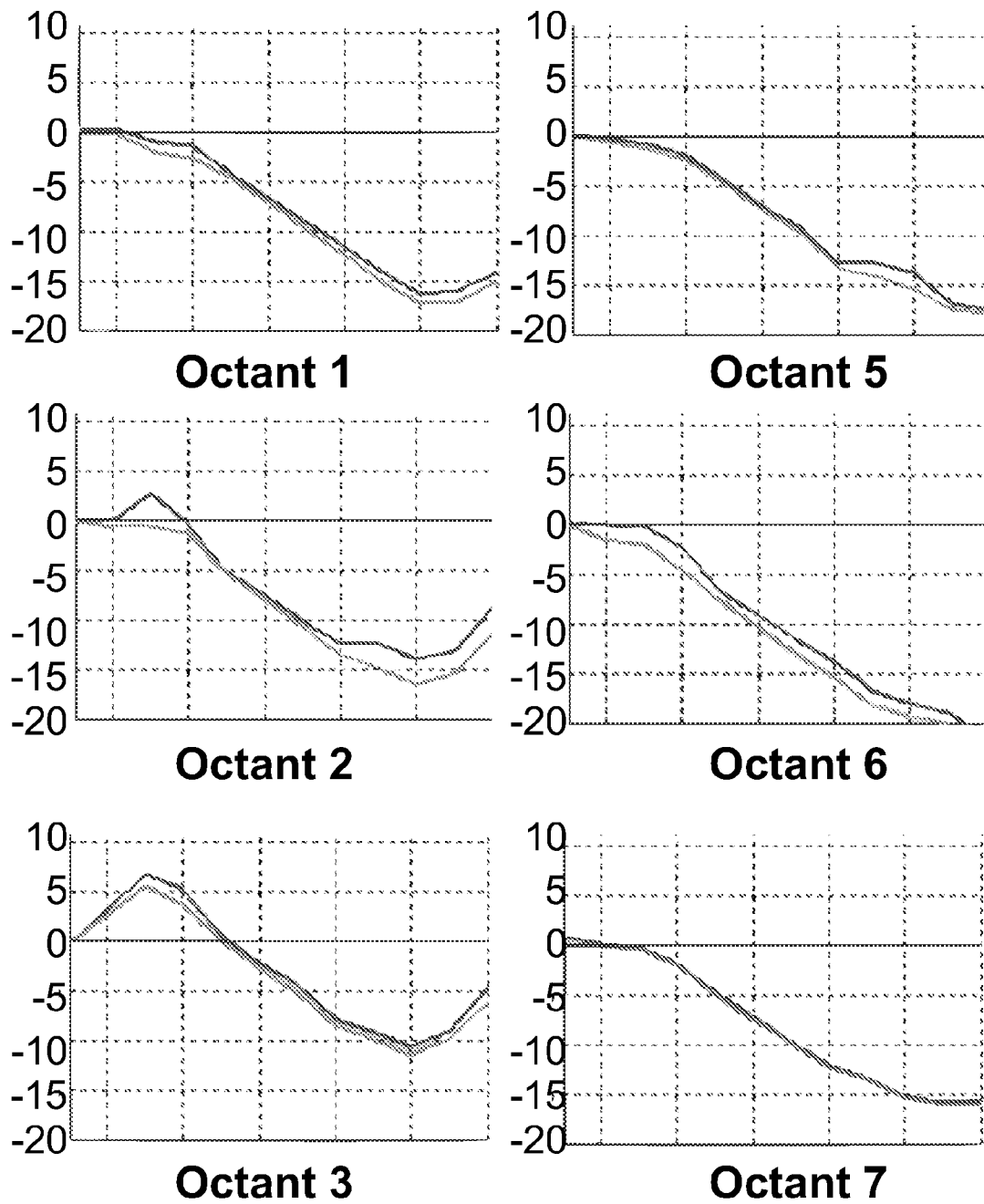
(b) Circumferential strain ($E_{CC}$) before correction (green) and after correction (red).
True $E_{CC}$ (compression) is less than the apparent
Fig. 16-b

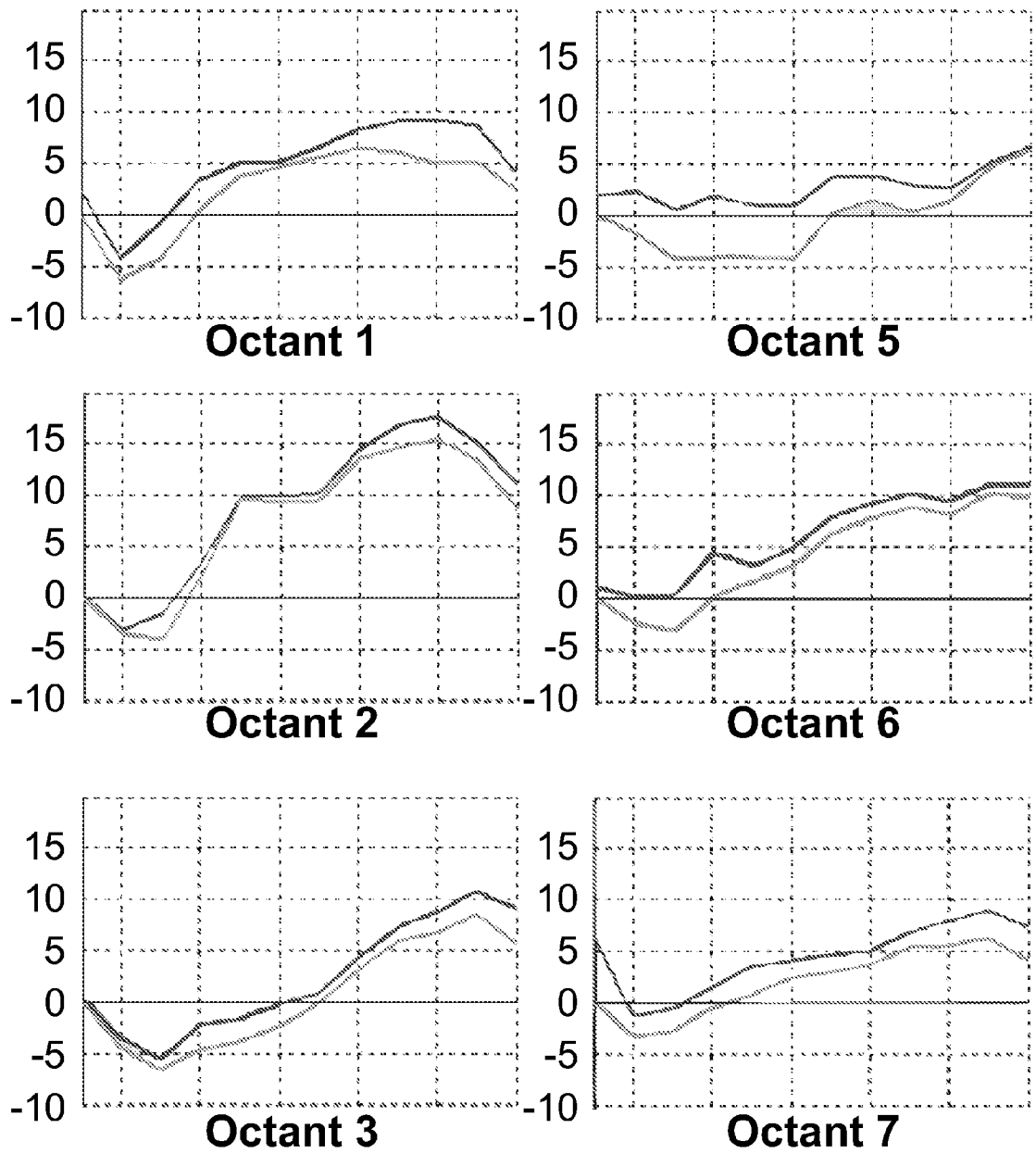
(c) Radial strain ($E_{rr}$) before correction (green) and after correction (red).
True $E_{rr}$ (thickening) is higher than the apparent
Fig. 16-c

THREE DIMENSIONAL MAGNETIC RESONANCE MOTION ESTIMATION ON A SINGLE IMAGE PLANE

CROSS REFERENCE TO RELATED APPLICATIONS

This application is a continuation of U.S. Non-Provisional Patent Application No. 11/418,563 filed on May 4$^{th}$, 2006 now U.S. Pat. No. 7,495,438, which claims priority to U.S. Provisional Patent Application No. 60/677,770 filed on May 4$^{th}$, 2005.

BACKGROUND

1. Field

Invention relates generally to tagged magnetic resonance imaging, and in particular to three-dimensional quantification without long image acquisition times and user-intensive post-processing methods.

2. Related Art

The use of magnetic resonance imaging (MRI) for the quantification of regional function of the heart based on the measurement of motion has great potential for clinical adoption. However, the primary limiting factors to date are the lengthy image acquisition protocols and tedious post-processing procedures required to yield regional motion measures.

Three main MRI protocols that have been used for the quantification of myocardial motion are myocardial tagging, displacement encoding with stimulated echoes (DENSE), and phase contrast (PC) velocity encoding techniques. See, generally, Aletras et al., "*DENSE: Displacement Encoding with Stimulated Echoes,*" Cardiac Functional MRI. J. Magn. Reson. 173 (1999) 247-252; Aletras et al., "*Mixed echo train acquisition displacement encoding with stimulated echoes: an optimized DENSE method for in vivo functional imaging of the human heart,*" Magn. Reson. Med. 46 (2001) 523-534; Pelc et al., "*Phase contrast cine magnetic resonance imaging,*" Magn. Reson. Q. 7 (1991) 229-254, and Pelc et al., "*Quantitative magnetic resonance flow imaging,*" Magn. Reson. Q. 10 (1994) 125-147.

In tagging, myocardial spins are modulated at end-diastole in a pre-specified pattern. Later in the cardiac cycle, the displaced taglines are imaged and tracked using post-processing algorithms in order to compute displacement and strain images. This technique permits rapid imaging and visualization as well as fast, automatic computation of in-plane (i.e. two-dimensional) motion measures using harmonic phase (HARP) processing. See, generally, Osman et al., "*Cardiac Motion Tracking Using CINE Harmonic Phase (HARP) Magnetic Resonance Imaging,*" Magn. Reson. Med. 42(6) (1999) 1048-1060, and Osman et al., "*Imaging heart motion using harmonic phase MRI,*" IEEE Trans. Med. Imag., 19(3) (2000) 186-202. To date, however, there has been no extension to three dimensions in an equally efficient and automatic way.

Phase contrast imaging adds to every myocardial spin a phase value proportional to the velocity in the encoding direction. PC imaging times are generally long and phase distortion leads to significant measurement errors. Also, since velocity rather than displacement is the measured quantity, computation of displacement and strain (as opposed to strain rate) at later times in a sequence is typically corrupted by numerical integration errors. PC is readily extended to three dimensions though imaging time becomes prohibitively long.

DENSE encodes position in a manner similar to MR tagging through the use of stimulated echoes. Automatic processing analogous to HARP can then be used to compute displacement and strain. The acquisition protocol of DENSE supports higher spatial resolution than that of conventional HARP techniques, but the computation of in-plane motion is sensitive to through-plane motion in DENSE, unlike conventional tagging techniques.

To date, extension of these three basic approaches to three dimensions has required extensive additional data collection over that of 2-D imaging. Furthermore, except for PC, the results yield only sparse motion information. In all three cases, long imaging times may be prohibitive due to patient breath-holding constraints or may produce sub-optimal results due to gross mis-registration of images collected over a long period of time.

As a result, no practical fully three-dimensional approach to the imaging of regional cardiac function is available. Accordingly, a need exists for imaging techniques and processing methods that overcome these difficulties.

SUMMARY

The above-described need has been met by the present invention.

A method for three-dimensional MR motion estimation on a single image plane (hereinafter also referred to as zHARP) based on tagged MRI and HARP processing. Tagged magnetic resonance imaging technique encodes and automatically tracks displacement of spatially modulated object in three dimensions, encoding both in-plane and through-plane motion in a single image plane without affecting acquisition speed. Post-processing unravels encoding in order to directly track 3-D displacement of points within the image plane throughout image sequence. The invention is particularly suited to use on a heart for tracking and determining myocardial displacement.

In one embodiment, an MR pulse sequence extends a slice-following complementary spatial modulation of magnetization (CSPAMM) pulse sequence with two small z-encoding gradients immediately before the readouts in successive CSPAMM acquisitions, thereby adding a through-plane encoding from which through-plane motion can be computed from acquired images. HARP processing is used to determine in-plane motion, after which through-plane position can be determined using phase encodings. Use of balanced encodings and horizontal and vertical tags permits cancellation of systematic phase artifacts present in CSPAMM acquisitions.

In another embodiment, a pulse sequence based on cosine and sine modulation to eliminate (CANSEL) artifact-generating echoes is used to obtain complete acquisition of zHARP data from an isolated spectral peak in five acquisitions, allowing artifact-free 3-D point tracking without phase mapping.

When used in a single image plane, zHARP yields a dense three-dimensional motion map of points in the plane and can be used to compute surface strain. When used with multiple image planes, zHARP tracks a rich collection of points within the myocardium and allows computation of fully 3-D measures of regional function, such as radial, circumferential, and longitudinal strain and twist, principal strains, or the direction of maximal thickening. ZHARP can also be used to compute a 3-D measure of global function, such as longitudinal shortening, rotation, or torsion.

It is an object of the present invention to compute dense 3-D motion from a single acquired image orientation without incurring an increase in imaging time over that of slice following CSPAMM.

It is a further object of the present invention to show consistent tracking performance throughout the time of tag persistence, in contract to the PC method where tracking errors accumulate over time.

It is a further object of the present invention to between in-plane strain and 3-D rotation, resolving an inherent ambiguity in 2-D HARP which cannot differentiate between in-plane strain and a simple 3-D rotation.

These and other objects of the invention will be more fully understood from the following description of the invention with reference to the drawings appended hereto.

BRIEF DESCRIPTION OF DRAWINGS

FIG. 4 illustrates displacement phase maps extraction for the experiment described in the first example below.

FIG. 10 illustrates data used in the experiment described in the third example below.

FIG. 16a, FIG. 16b, and FIG. 16c illustrate results obtained in a healthy adult subject as described in the fourth example below.

DETAILED DESCRIPTION

As employed herein, the term "patient" shall mean a living member of the animal kingdom including human beings.

As employed herein, the term "object" shall mean a portion of a patient which is the subject of dynamic motion with respect to other portions of the body or with respect to the surroundings of the body and shall expressly include, but not be limited to, the heart and portions thereof, muscles, tongue, cerebrospinal fluid, and the brain.

Tagged MRI uses an MR scanner to temporarily change the magnetic properties in and around the heart in a pre-specified pattern, which can the be imaged as both the heart and the pattern undergo deformation. Analysis of the deformed patterns in the resulting image sequence yields information about the motion of the heart muscle within its walls.

The present invention (zHARP) discloses MRI techniques for imaging and automatically tracking the 3-D displacement of points in an image plane, such as myocardial points. A pulse sequence for acquiring an image that encodes both in-plane and through-plane motion without affecting the acquisition speed of the underlying pulse sequence is presented. Also presented are methods, based on the harmonic phase (HARP) concept, which track the 3-D displacements of points in the image plane through the image sequence. The presented methodology is validated in both phantom and human studies.

Pulse Sequence

To measure the motion of an object by magnetic resonance imaging, a region of interest in the object is spatially modulated using a slice-following 3-D tagging imaging sequence (pulse sequence). The pulse sequence used in the present invention is based on a standard slice-following CSPAMM (SF-CSPAMM) sequence (see, generally, Fischer et al., "*True Myocardial Motion Tracking*," Magn. Reson. Med. 31 (1994) 401) but with the addition of a z-encoding gradient applied twice before the read-out to the second orthogonal CSPAMM acquisition, wherein the z-encoding gradient is applied with opposite polarity the second time around.

Figure 1:
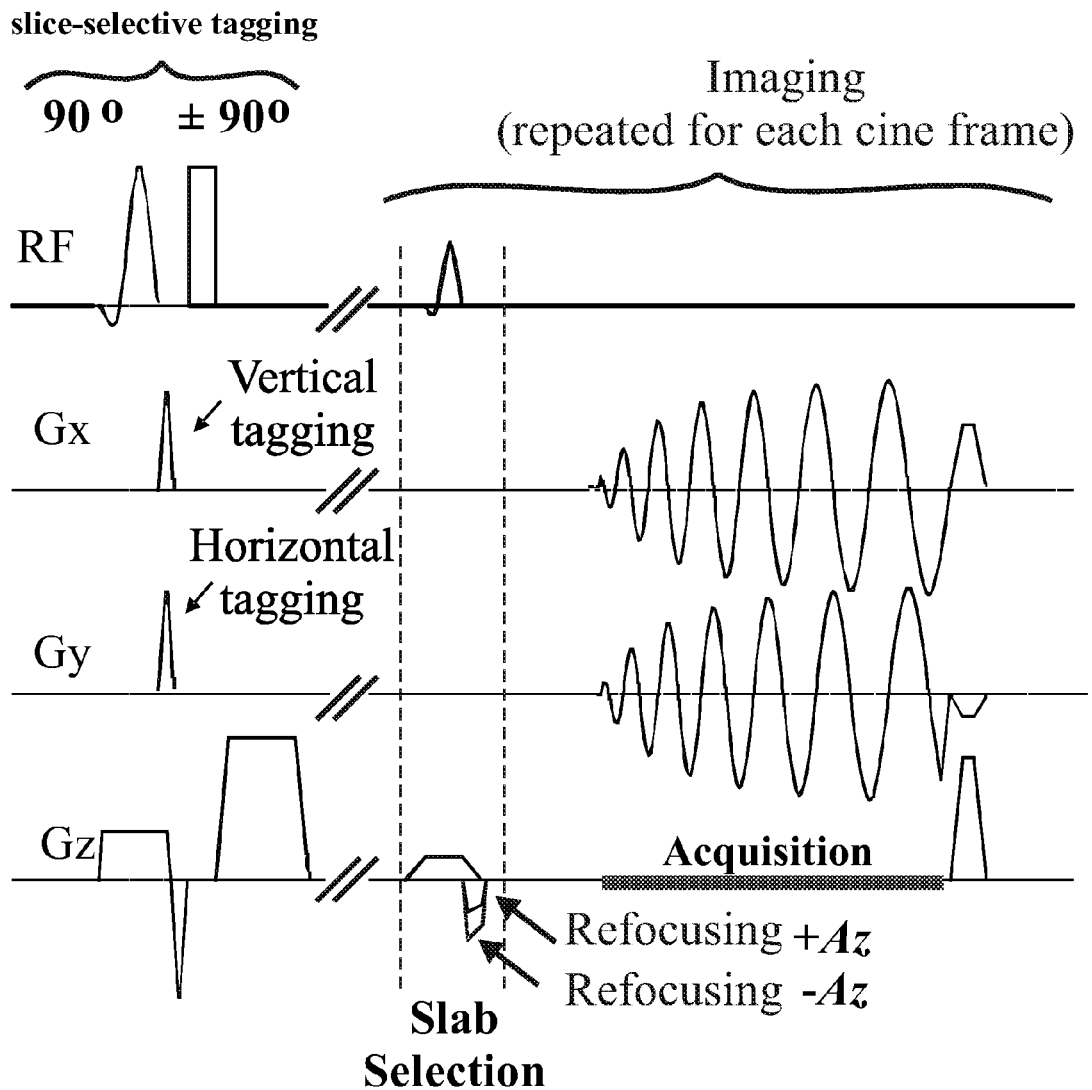
FIG. 1 illustrates a zHARP pulse sequence.

FIG. 1 illustrates a zHARP pulse sequence, showing a typical CSPAMM tagging spiral acquisition sequence with an added z-encode gradient with magnitude $|A_z|$ in the slice-select direction. A+$A_z$ gradient and a–$A_z$ gradient are added to vertical and horizontal tagging sequences, respectively. The gradient adds a z-position dependent phase $\phi_z$ to material points in an acquired slice. This additional phase is linearly related to the distance of the point from the isocenter of the scanner. While susceptibility and general field inhomogeneities lead to an additional (artifactual) phase accumulation $\phi_e$, this erroneous phase is identical in both the horizontally and vertically tagged images and will be shown to (mathematically) vanish in the computation of in-plane and through-plane displacements.

ZHARP Formulation

The zHARP z-encode gradient has the same strength for A and B CSPAMM acquisitions. Upon complex signal acquisition and subtraction, the signal from the untagged tissue is removed, similar to standard CSPAMM. However, the tagged tissue now has a z-phase, acquired at the imaging moment. Accordingly, the z-encoded CSPAMM image I (r, t) at r(x, y) and time t can be represented as $$I(r, t) = 2 \int_{\bar{z}(r)-\Delta/2}^{\bar{z}(r)+\Delta/2} \rho(r, t) e^{j\varphi_e(r)} \cos(\omega^T p(r, t)) e^{j\kappa_z(r)z(r)} \, dz \quad (1)$$

wherein $\bar{z}$ is the (tag) slice position, $\Delta$ is the (tag) slice thickness, $\rho(r, t)$ is the effective spin density, $\omega$ is the tag frequency, $p(r, t)$ is the reference map (the position of the 3-D spatial point r at the reference time), and $\kappa_z$ is the z-encode frequency.

If the frequency $\kappa_z$ is small enough and the slice thin enough, we obtain the approximation $$I(r,t) \approx 2\rho(r,t) e^{j\phi(r)} \cos(\omega^T p(r,t)) e^{j\kappa_z(r)\bar{z}(r)} \quad (2)$$

Letting $\phi_z(r) = \kappa_z(r)\bar{z}(r)$, (2) becomes $$I(r,t) \approx 2\rho(r,t) e^{j\phi_e(r)} e^{j\phi_z(r)} \cos(\omega^T p(r,t)). \quad (3)$$

This is the commonly known CSPAMM image multiplied by $e^{j\Phi_e(r)}e^{j\Phi_z(r)}$, which means that the $\bar{z}$ positions of myocardial material points in the slice are now encoded in the phase of the complex image I without affecting the usual CSPAMM magnitude content. For simplicity of notation in the following, we omit the argument of $\phi_e(r)$ and $\phi_z(r)$.

ZHARP Images

An image plane is scanned twice in order to compute the in-plane motion, first with vertical tagging $\omega = \phi_x (1,0,0)$, and then with horizontal tagging $\omega = \omega_y (0,1,0)$. A positive z-encode gradient is applied to the first scan and a negative z-encode gradient is applied to the second scan. Using the relation $$p(r,t) = r - u(r,t), \tag{4}$$

wherein u is the displacement, (3) becomes $$I_x(r,t) \propto \rho(r,t) e^{j\Phi_e} e^{j\Phi_z} \cos(\omega_x x - \omega_x), \tag{5}$$

$$I_y(r,t) \propto \rho(r,t) e^{j\Phi_e} e^{-j\Phi_z} \cos(\omega_y y - \phi_y), \tag{6}$$

for the first and second scans, wherein $\phi_x = \phi_x u_x$ and $\phi_y = \omega_y u_y$. In these equations, the phases $\phi_x$ and $\phi_y$ are called either the displacement-encoding phases or the harmonic phase (HARP) maps in the x and y directions, respectively. See, generally, Osman et al, "*Imaging heart motion using harmonic phase MRI*," IEEE Trans. Med. Imag., 19(3)(2000) 186-202. It is noted that grid tags may be used as well, in which case they may have both the vertical and horizontal tags and the acquired images will be grid tagged images. The grid tagged images may be vertically and horizontally tagged, or they may be tagged in any two orthogonal directions.

Two steps are used to extract the 3-D displacement of a material point.

Step 1: Extraction of displacement-encoding phase maps. Although at first glance it may appear impossible to sort out the in-plane and through-plane motion components from the image data in (5) and (6), it can nevertheless be accomplished by applying the 2-D HARP concept (see, generally, Osman et al, "*Imaging heart motion using harmonic phase MRI*," IEEE Trans. Med. Imag., 19(3)(2000)186-202, and Osman et al., "*Cardiac Motion Tracking Using CINE Harmonic Phase (HARP) Magnetic Resonance Imaging*," Magn. Reson. Med. 42(6)(1999)1048-1060) to the negative and positive harmonic peaks of $I_x$ and $I_y$. This idea is illustrated in the block diagram of FIG. 2a, and FIG. 2b. Whereas in conventional HARP there would be only two harmonic phases that are computed, one for the horizontally tagged image and one for the vertically tagged image, the present invention computes four harmonic phases, $\phi_A, \phi_B, \phi_C,$ and $\phi_D$. Furthermore, these computed phases include not only the harmonic phases, $\phi_x$ and $\phi_y$ arising from object in-plane motion, but also a phase $\phi_z$ arising from the explicit z-encoding and a phase $\phi_e$ arising from erroneous phase sources.

Figure 2:
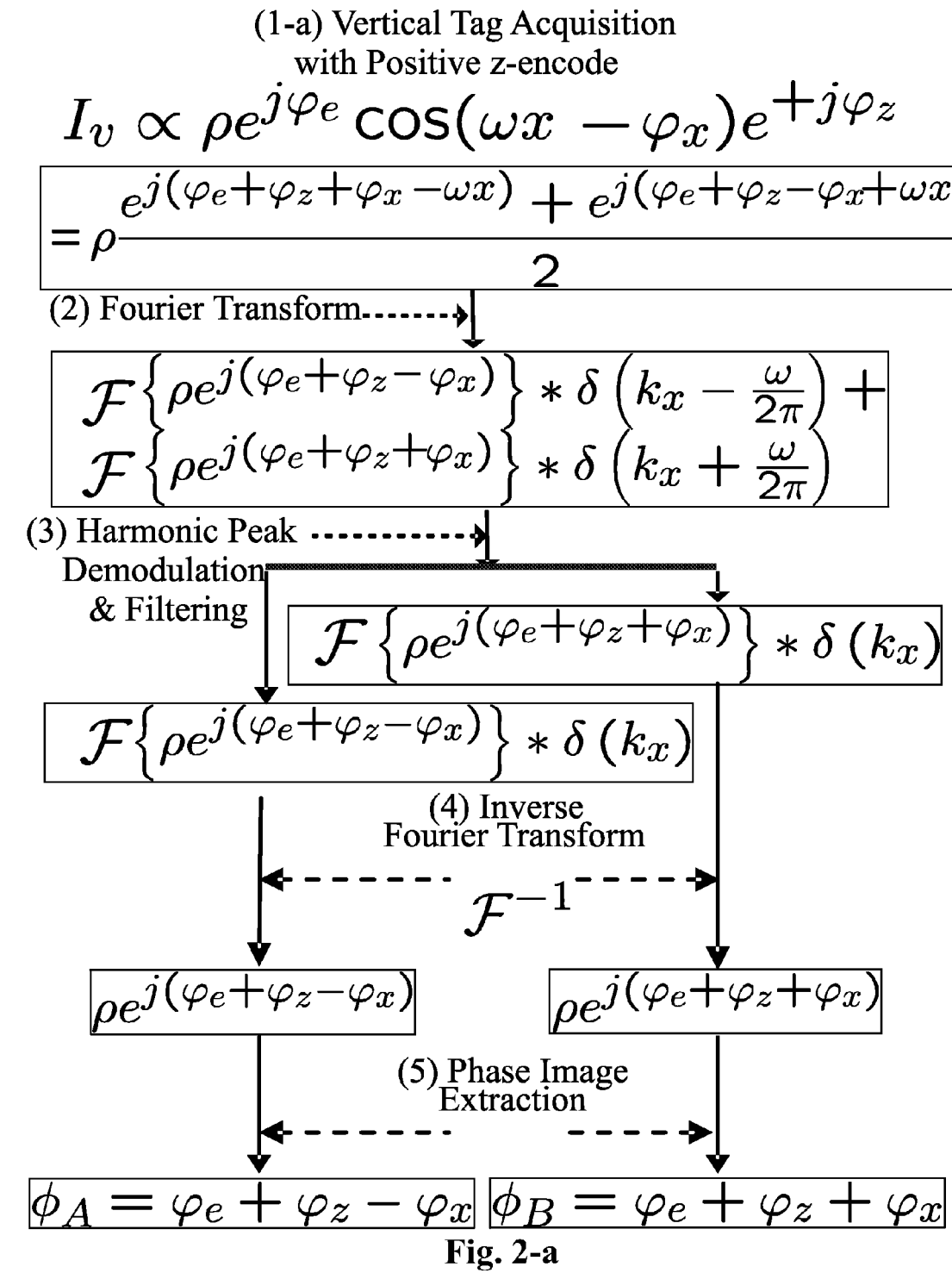
FIG. 2a and FIG. 2b illustrate extraction of displacement-encoding phase maps.

FIG. 2a and FIG. 2b illustrate extraction of displacement-encoding phase maps, with FIG. 2a flowchart showing the extraction of $\phi_A$ and $\phi_B$ of from vertically tagged images $I_x$, and FIG. 2b flowchart showing the extraction of $\phi_C$ and $\phi_D$ of from horizontally tagged images $I_y$. The * and δ symbols represent linear convolution and the impulse function, respectively. The computed harmonic phases form the following system of linear equations:

$$\phi_A = \phi_e + \phi_z - \phi_x, \tag{7}$$

$$\phi_B = \phi_e + \phi_z + \phi_x, \tag{8}$$

$$\phi_C = \phi_e - \phi_z - \phi_y, \tag{9}$$

$$\phi_D = \phi_e - \phi_z + \phi_y. \tag{10}$$

This system is readily solved for the desired phases that are related to motion, yielding $$\phi_x = (\phi_B - \phi_A)/2, \tag{11}$$

$$\phi_y = (\phi_D - \phi_C)/2, \tag{12}$$

$$\phi_z = ((\phi_A - \phi_B) - (\phi_C - \phi_D))/4. \tag{13}$$

Step 2: 3-D Motion Tracking. Consider a material point located at $r_m$ at time $t_m$. The principle of 2-D HARP tracking (see, generally, Osman et al., "*Cardiac Motion Tracking Using CINE Harmonic Phase (HARP) Magnetic Resonance Imaging*," Magn. Reson. Med. 42(6)(1999)1048-1060) is based on the fact that HARP phase is a material property, and therefore that the apparent in-plane position of this point at time $t_{m+1}$, given by $r_{m+1}$, can be determined by the following relations:

$$\phi_x(r_{m+1}, t_{m+1}) = \phi_x(r_m, t_m), \tag{14}$$

$$\phi_y(r_{m+1}, t_{m+1}) = \phi_y(r_m, t_m). \tag{15}$$

Now consider a point on the image plane $r_0$ at the time $t_0$ of tag application. Since the phases $\phi_x$ and $\phi_y$ are found using (11) and (12), 2-D HARP tracking can be used to track the apparent in-plane position of $r_0$ throughout the image sequence (see, generally, Osman et al, "*Imaging heart motion using harmonic phase MRI*," IEEE Trans. Med. Imag., 19(3) (2000)186-202). This yields a sequence of points in the image plane given by $\{r_0, \ldots, r_m, r_{m+1}, \ldots\}$. This is a standard HARP result, a tracking of the apparent 2-D position of an arbitrary point in the plane. Advantageously, using the present invention this result can be obtained despite the presence of an explicit z-encode and the presence of phase anomalies.

Because slice following is used, it is now possible to recover the z position of $r_0$ throughout the sequence. At the time of tag (and z-encode) application, we have $$\phi_z(r_0, t_0) \approx \kappa_z z_0. \tag{16}$$

At a later time, if the z phase does not wrap, we have the relation $$\phi_z(r_{m+1}, t_{m+1}) - \phi_z(r_m, t_m) \approx \kappa_z(z_{m+1} - z_m). \tag{17}$$

Rearranging, and using the wrapping operator W as defined in above-referenced Osman et al, "*Imaging heart motion using harmonic phase MRI*" (which recovers the correct net phase difference), yields $$z_{0+1} = z_0 + \frac{1}{\kappa_z} W\{\varphi_z(r_{m+1}, t_{m+1}) - \varphi_z(r_m, t_m)\}, \tag{18}$$

which can be used in an iterative fashion to track the z position of $r_0$ throughout the sequence.

Together, the above two steps describe the algorithmic component of zHARP. It should be obvious to one of ordinary skill in the art that a single point or an arbitrary collection of points in an image slice can be tracked in three dimensions using this imaging and processing methodology.

In another embodiment, a pulse sequence based on cosine and sine modulation to eliminate (CANSEL) artifact-generating echoes is used to obtain complete acquisition of zHARP data from an isolated spectral peak in five acquisitions, allowing artifact-free 3-D point tracking without phase mapping.

In order to confirm the effectiveness of the methods of the present invention, experiments were performed on phantoms and a normal human volunteer. Quantitative comparisons between zHARP and prior art tag tracking methods are made.

EXAMPLE 1

1-D z Displacement of Phantom

Figure 3:
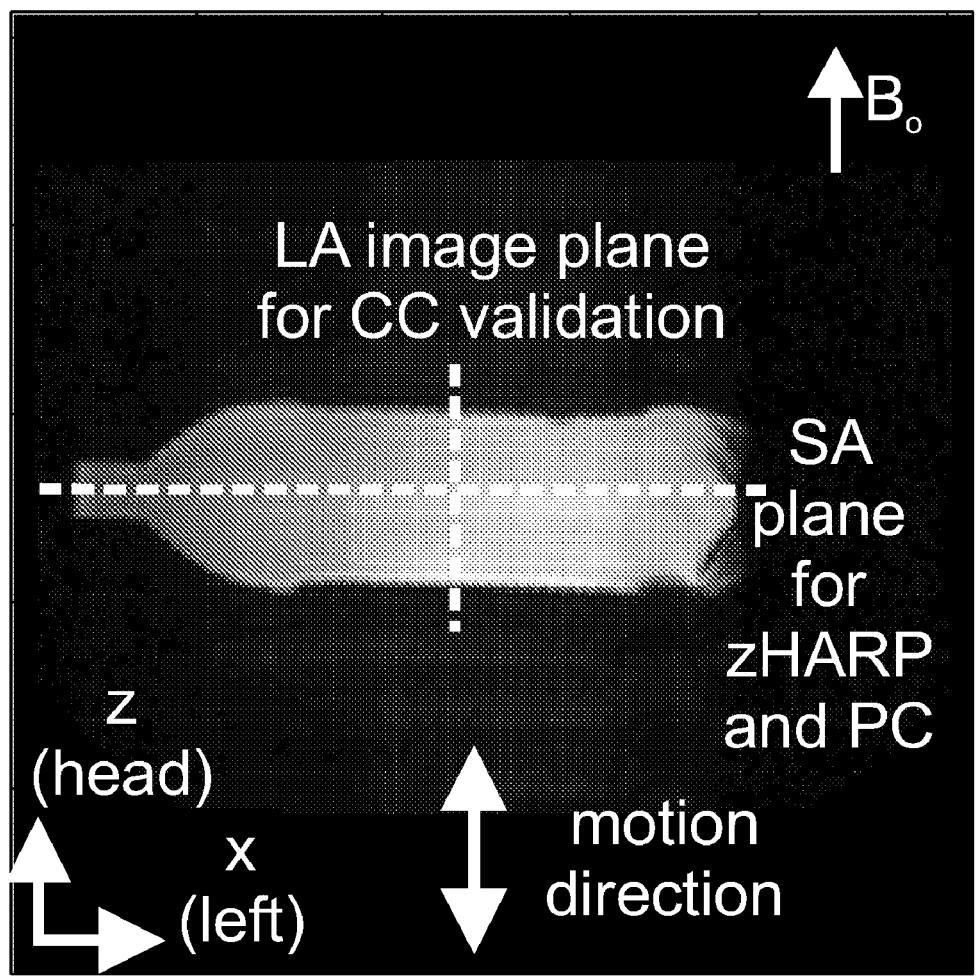
FIG. 3 illustrates short axis (SA) and long axis (LA) slice orientations for an experiment described in the first example below.

The pulse sequence and the algorithm were tested on a water-filled-bottle phantom moving sinusoidally (1" peak-to-peak) in parallel to the main magnetic field (z direction) at a rate of 52 cpm. The orientations of the acquired slice, so-called short axis (SA) slice, as well as the long axis (LA) slice are shown in FIG. 3. Motion is along the $B_0$ field of the magnet. SA slice is along the bottle axis of symmetry and perpendicular to the direction of motion. LA slice is perpendicular to axis of symmetry. Fourteen axial-plane cardiac phases were acquired during the first 466 ms of each cycle. FIG. 4 shows the zHARP algorithm steps applied to the 14$^{th}$ frame and how the through-plane and in-plane displacements were extracted. In this experiment, though-plane displacement occurred and was measured. Phase maps are shown at a rectangular region of interest (ROI) in the middle of the bottle. The magnitude image of the bottle is shown in the background of the ROI.

Figure 5:
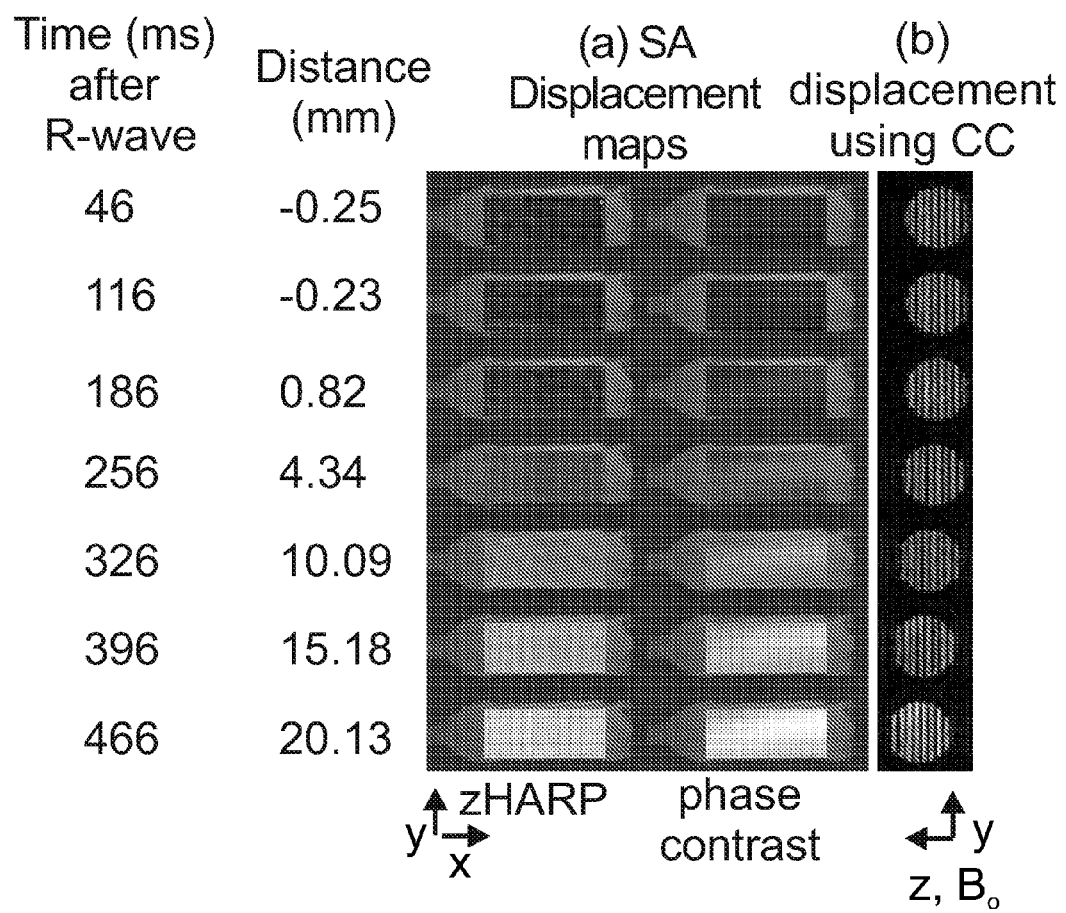
FIG. 5 illustrates z displacement maps extraction for the experiment described in the first example below.

For comparison, the phantom was also imaged using a conventional PC method and a z displacement map was obtained thereafter by integration. FIG. 5 illustrates z displacement ($\phi_z$) maps extraction for the experiment through the 14 CINE images, wherein t represents time, d represents displacement, and column (a) on the left shows maps using zHARP and on the right shows maps using PC. As a reference standard, z displacement was also computed using a cross correlation (CC) method applied to the LA tagged dataset, and column (b) shows a reference standard dataset with tagged long axis slices used for displacement calculations using the CC method.

Figure 6:
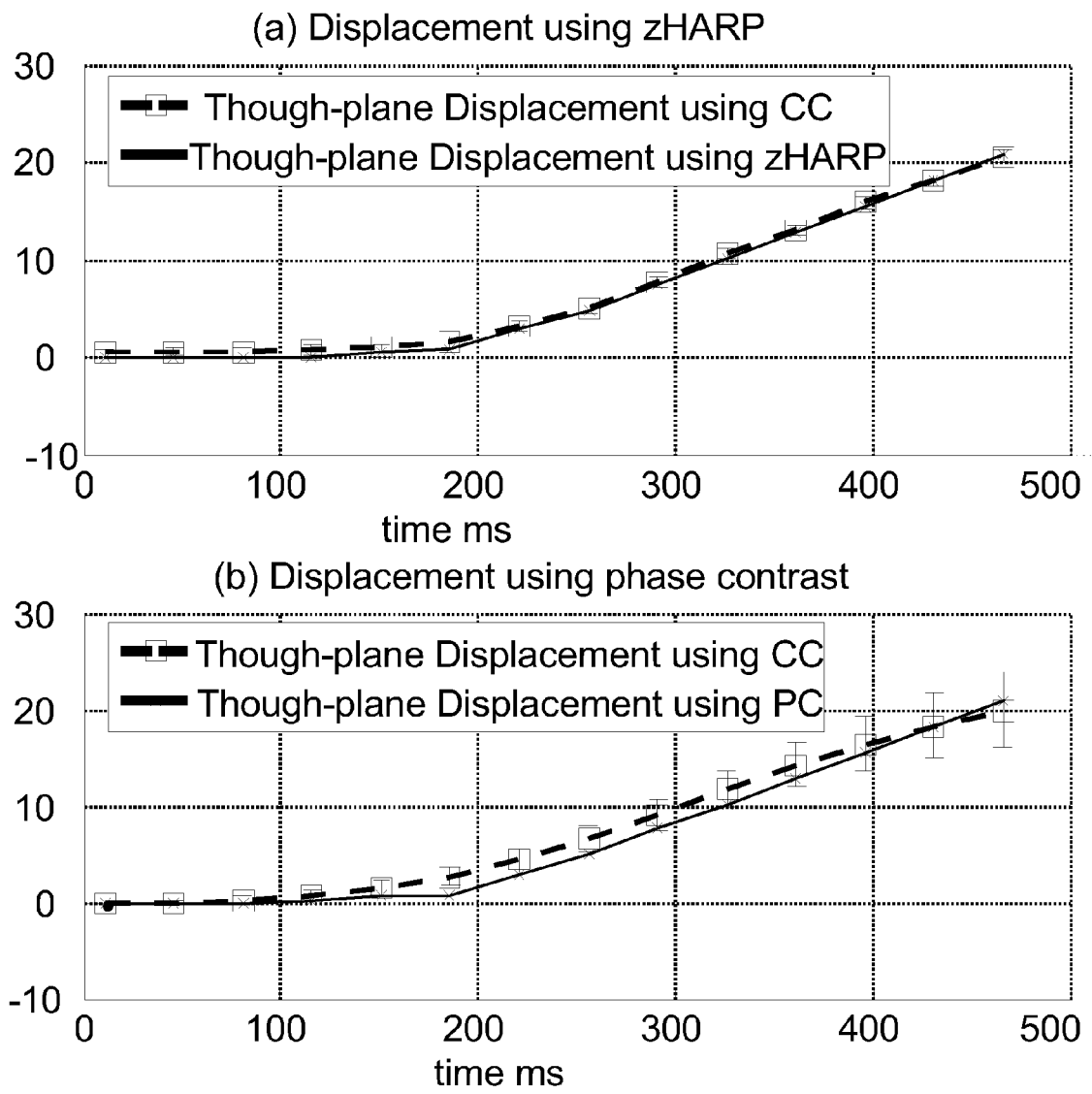
FIG. 6 illustrates z displacement profile in the first 460 ms of a phantom motion cycle for the experiment described in the first example below.

Through-plane motion in the SA slice is shown as in-plane horizontal shift in the LA slice as shown in FIG. 5. FIG. 6 compares the mean displacement value and the standard deviation obtained from PC, zHARP, and CC. Relative RMS error between PC and CC was 10.7% and between zHARP and CC was only 4.0%. FIG. 6 shows the z displacement ($\phi_z$) profile in the first 460 ms of the phantom motion cycle, with graph (a) showing the displacement using zHARP and graph (b) showing displacement using PC, illustrating increasing standard deviation and drift of the PC values from the cross correlation values.

EXAMPLE 2:

2-D Combined x and z Displacement

Figure 7:
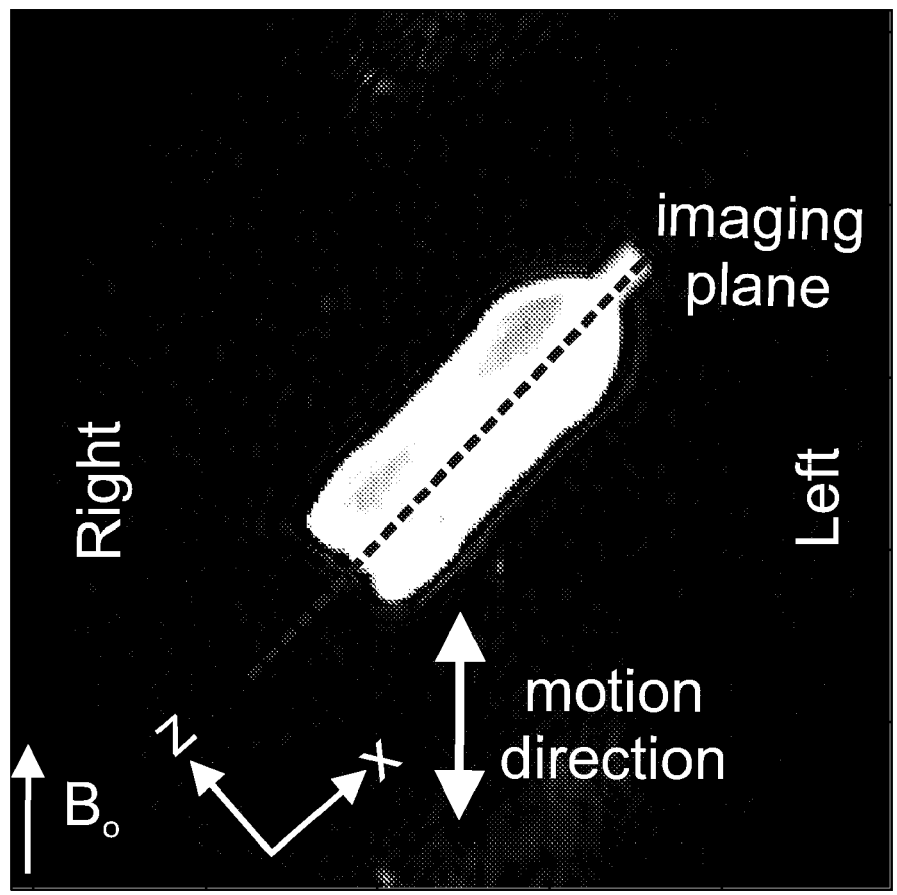
FIG. 7 illustrates short axis (SA) and long axis (LA) slice orientations for the experiment described in the second example below.

In the second experiment, the phantom and the imaged slice were tilted by 43° about the anterior-posterior axis while the phantom was moving along the $B_0$ field direction. In addition, a stationary water phantom was inserted above the imaging coil for comparison. In this tilted placement, both in-plane x displacement and through-plane z motion components were generated. FIG. 7 illustrates short axis (SA) and long axis (LA) slice orientations for the experiment.

Figure 8:
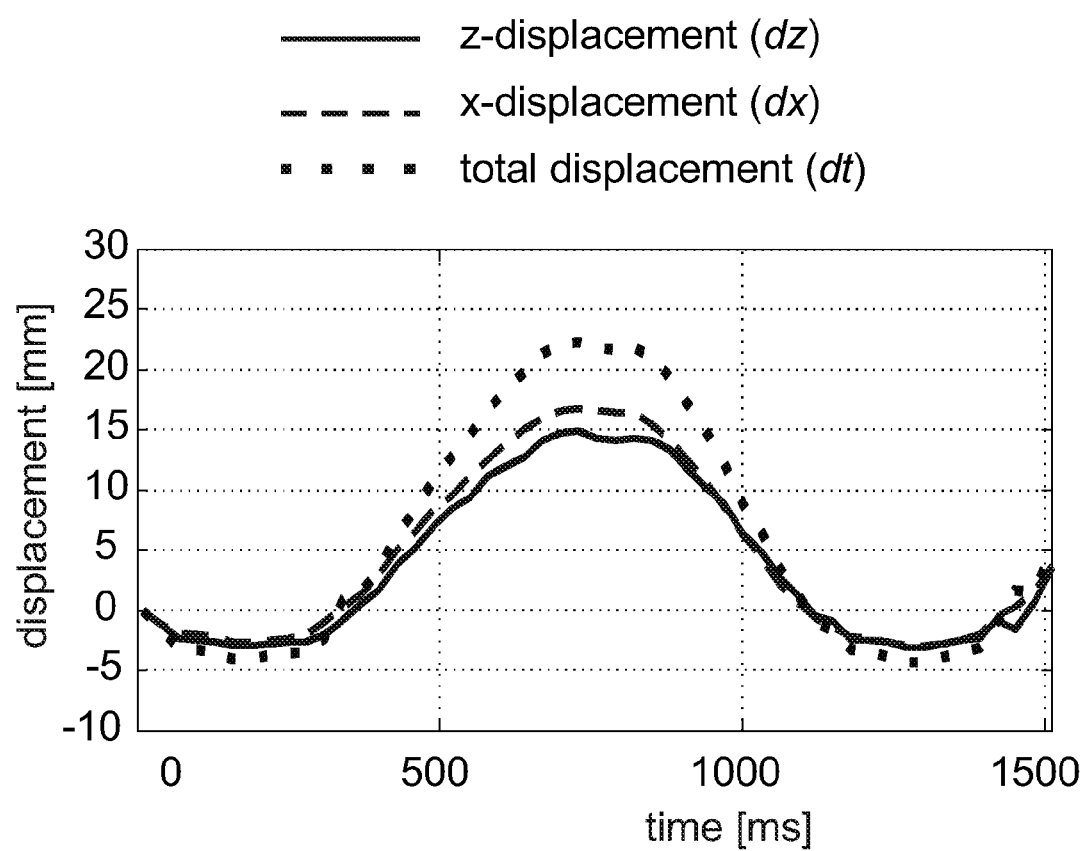
FIG. 8 shows the displacement profile through a motion cycle for the experiment described in the second example below.

FIG. 8 shows the displacement profile through a motion cycle, illustrating average in-plane and through-plane displacement profiles with time and the total 1" peak-to-peak displacement. Both x and z displacement maps are shown and, as expected, both displacements follow a sinusoidal pattern. Because of the tilting-setup, |mean(x displacement)|=tan(43°)×|mean(z displacement)| at any time. The total displacement profile $\sqrt{|\text{z-displacement}|^2+|\text{x-displacement}|^2}$ is shown with 1" peak-to-peak total displacement as expected.

Figure 9:
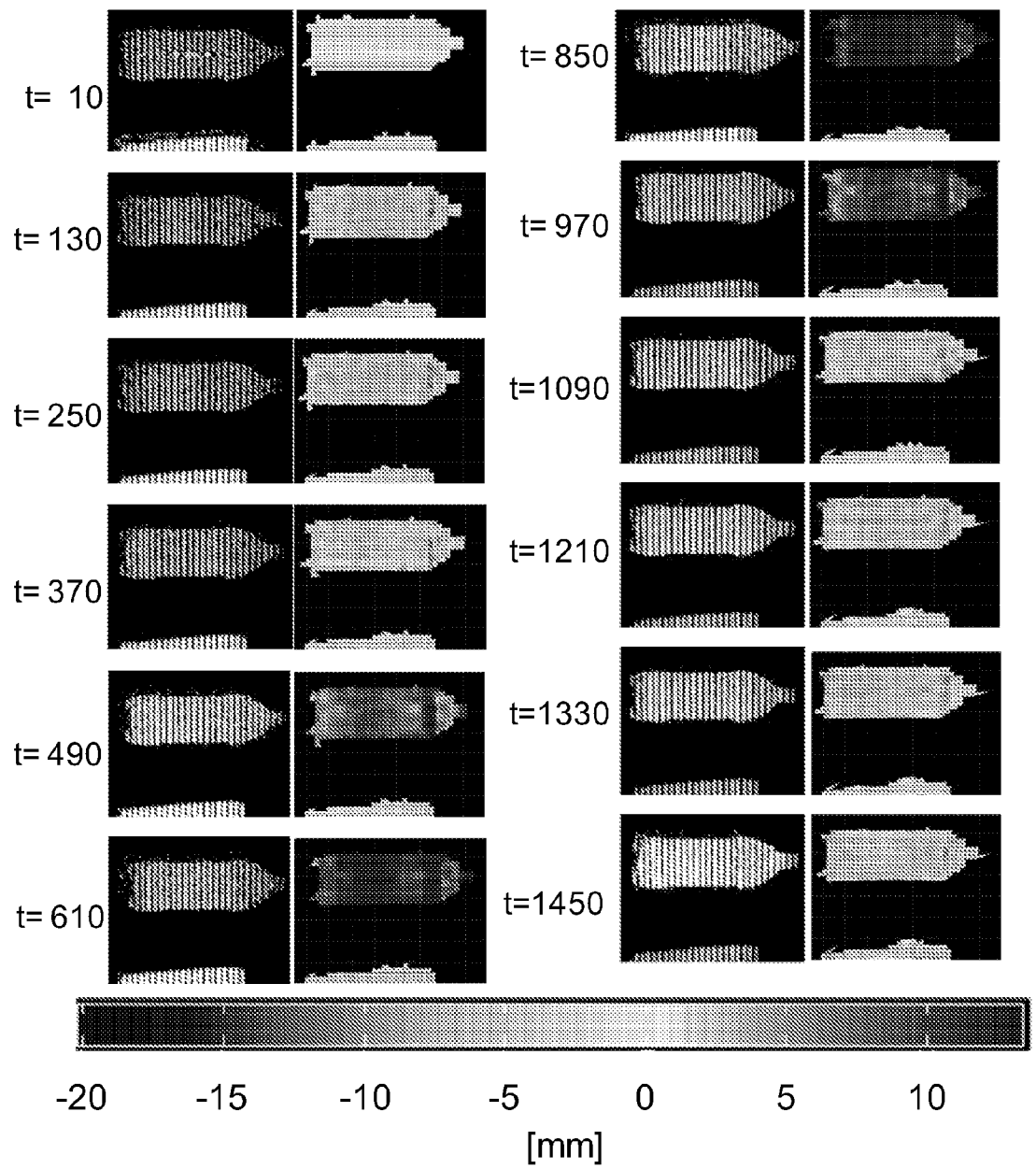
FIG. 9 illustrates tracking results of sample time-frames for the experiment described in the second example below.

A rectangular mesh of points was constructed over the stationary and moving phantoms and tracked throughout the cycle. Tracking results of sample time-frames are shown in FIG. 9 illustrating SA CINE time-frames and tracking. The left shows sample tagged images at different time instants of the motion cycle (notice the horizontal motion of the phantom). The middle shows the corresponding zHARP mesh tracking, with in-plane tracking shown as a shift in the phantom position from frame to frame and through-plane tracking shown as a change in coloring. The right shows the color palette used for representing through-plane motion tracking.

The frames show both an SA slice in the moving phantom (in the center of the image) and a part of the stationary phantom (at the bottom of the image). Notice the yellow color of the stationary phantom and the change of the moving phantom from yellow (z=0) to green (z=−υe) then to red (z=+υe) then to green (z=−υe) (compare with the profile in FIG. 8).

EXAMPLE 3

Normal Volunteer

The following data was obtained from a 26-year-old healthy adult male subject with a heart rate of approximately 80 bpm. Four ECG leads were placed on the chest for triggering of the pulse sequence by the R-wave. The patient position was head first and supine. An oblique, equatorial short-axis, 6 mm-thick slice of the left ventricle was scouted. FIG. 10(*a*) shows the location and orientation of a four-chambers slice (4C). The line shown is the intersection between the shown 4C and the acquired SA slice. Twelve systolic images of size 256×256 were acquired starting from end-diastole to end-systole with a square FOV of 35 cm and temporal resolution of 30 ms. The first and last time-frames were scanned 11 ms and 341 ms, respectively, after the R-wave trigger. FIG. 10(*b*) shows the twelve 97×97 LV region-of-interest (ROI) datasets as they appear in the acquired horizontal tag zHARP.

Figure 11:
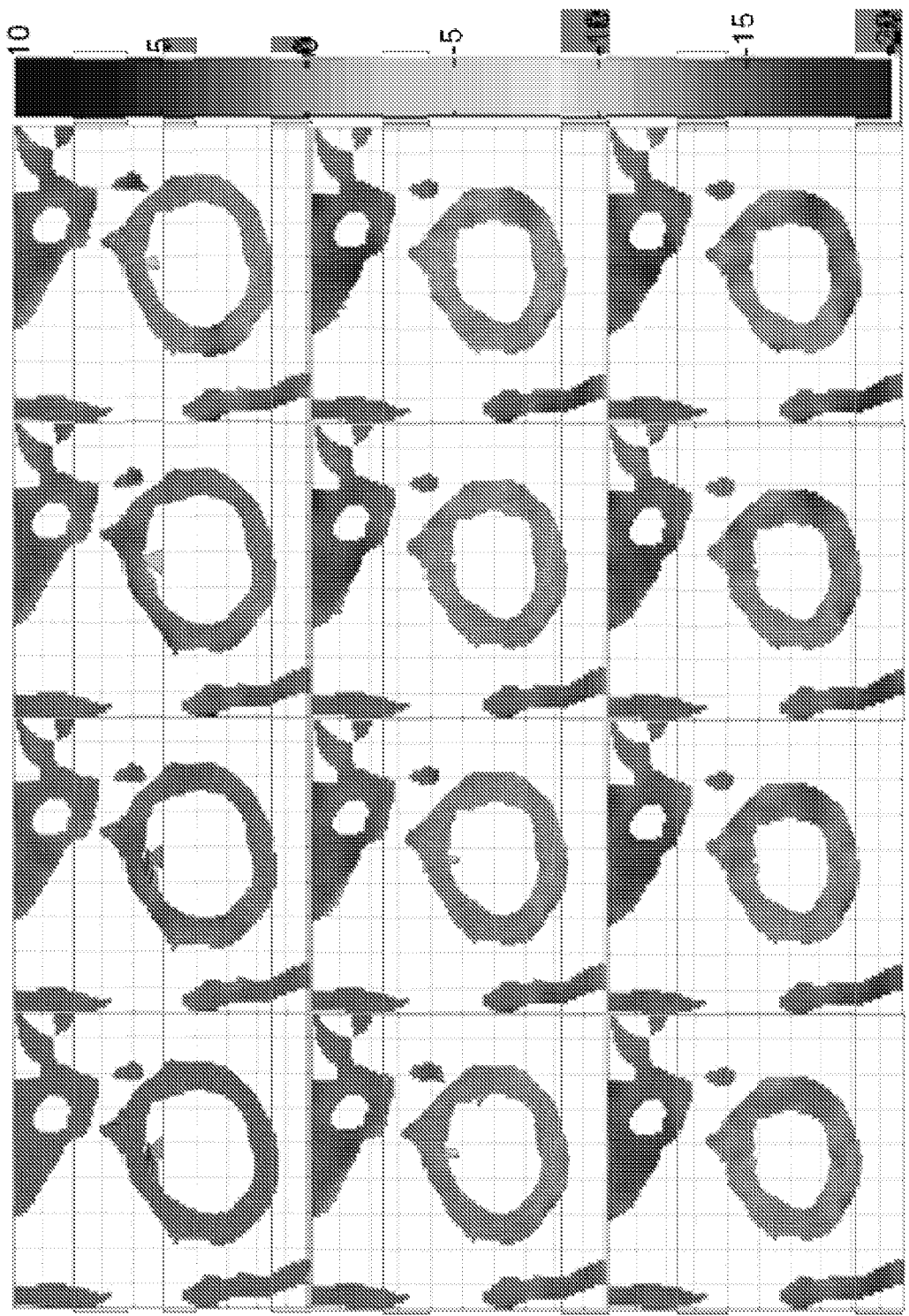
FIG. 11 illustrates a mesh tracking result, with in-plane displacements shown as twisting and binding of the mesh grid lines, and through-plane displacement shown as colors of the points.
Figure 12:
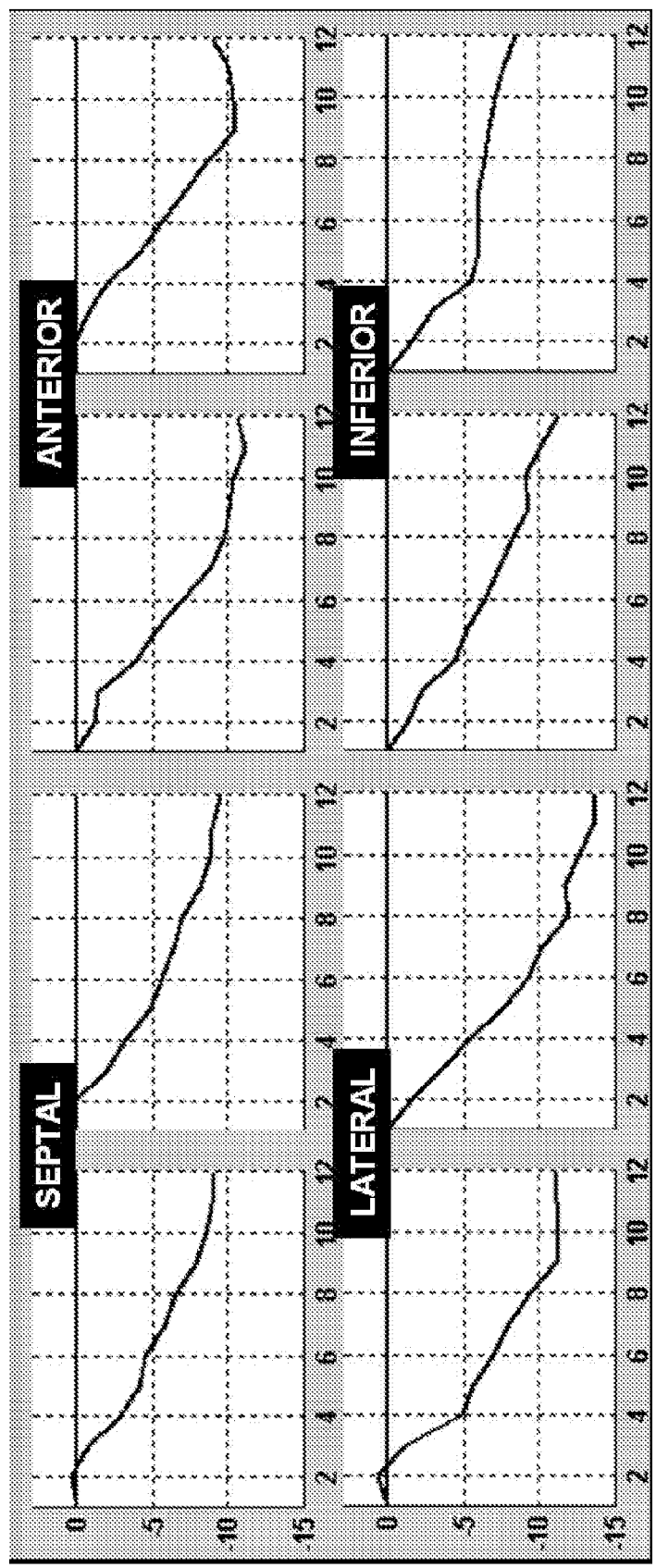
FIG. 12 illustrates z displacement tracking results for points around the myocardium for the experiment described in the third example below.

A 97×97 mesh of points was tracked on the ROI data. Results in FIG. 11 show in-plane twisting of the mesh and color-encoded z displacement. FIG. 12 shows the though-plane displacement profile of selected tracked points around the LV myocardium, with vertical axes in mm and horizontal axes representing the time-frame index.

Combining the techniques of the present invention with a multi-slice acquisition provides a layer-cake of 3-D tracked points which can be used to track the heart and compute a variety of strains, thereby allowing to significantly reduce the number of planes that are acquired, and still obtain an accurate assessment of the state of the LV and RV myocardium.

Resolving Through-Plane Rotation Ambiguity

It is a further advantage of the present invention that it resolves an inherent ambiguity in 2-D HARP that prevents differentiating between an in-plane strain and a simple 3-D rotation. When quantitative strain maps are calculated for a cardiac imaging plane after an image slice is acquired using functional cardiac MRI methods, such as tagging (see, generally, Axel et al., "*Heart wall motion: improved method of spatial modulation of magnetization for MRI,*" Radiology 1989; 172:349-350), displacement encoding (see, generally, Pelc et al., "*Tracking of cyclic motion with phase-contrast cine MR velocity data*", J Magn Reson Imaging 1995 May-Jun; 5(3):339-45), or velocity encoding (see, generally, Aletras et al, "*DENSE: displacement encoding with stimulated echoes in cardiac functional MRI*," J Magn Reson. 1999 Mar; 137(1):247-52.), as a result of through-plane motion the imaged slice may not necessarily be the same slice that was motion-encoded, which may cause the computed strain to be inaccurate. With slice-following tagging (see, generally, Fischer et al., "*True myocardial motion tracking*," Magn Reson Med. 1994 Apr; 31(4):401-13), the same tissue of the myocardium is always examined. However, through-plane rotation can still be misinterpreted as a false strain. As a result, only the in-plane motion and apparent strain can be computed when only a single slice is imaged. In contrast, the method of the present invention provides a true planar strain map for a given imaged slice by taking the through-plane motion into consideration and correcting for the false strain component caused by through-plane rotation.

Figure 13:
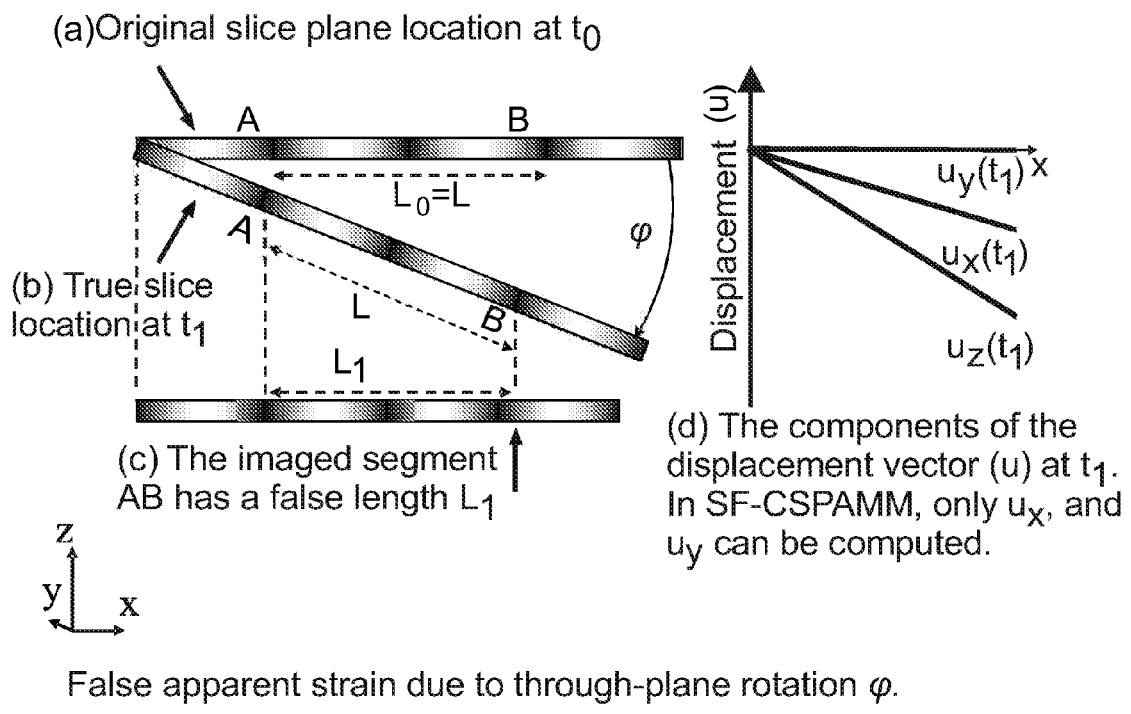
FIG. 13 illustrates an example of false apparent strain due to through-plane motion.
Figure 14:
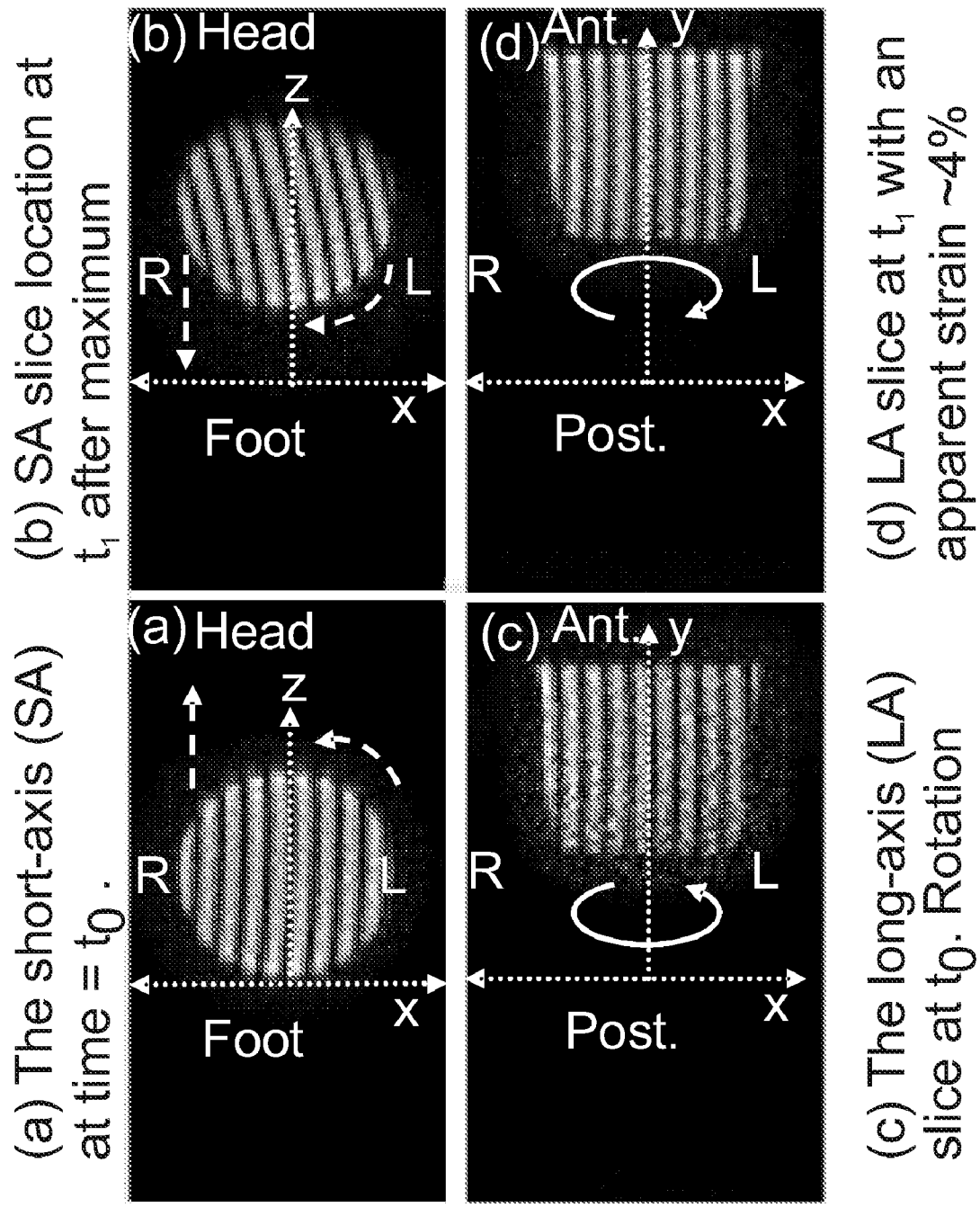
FIG. 14 illustrates some images acquired using the cylindrical phantom experiment described in the fourth example below.
Figure 15:
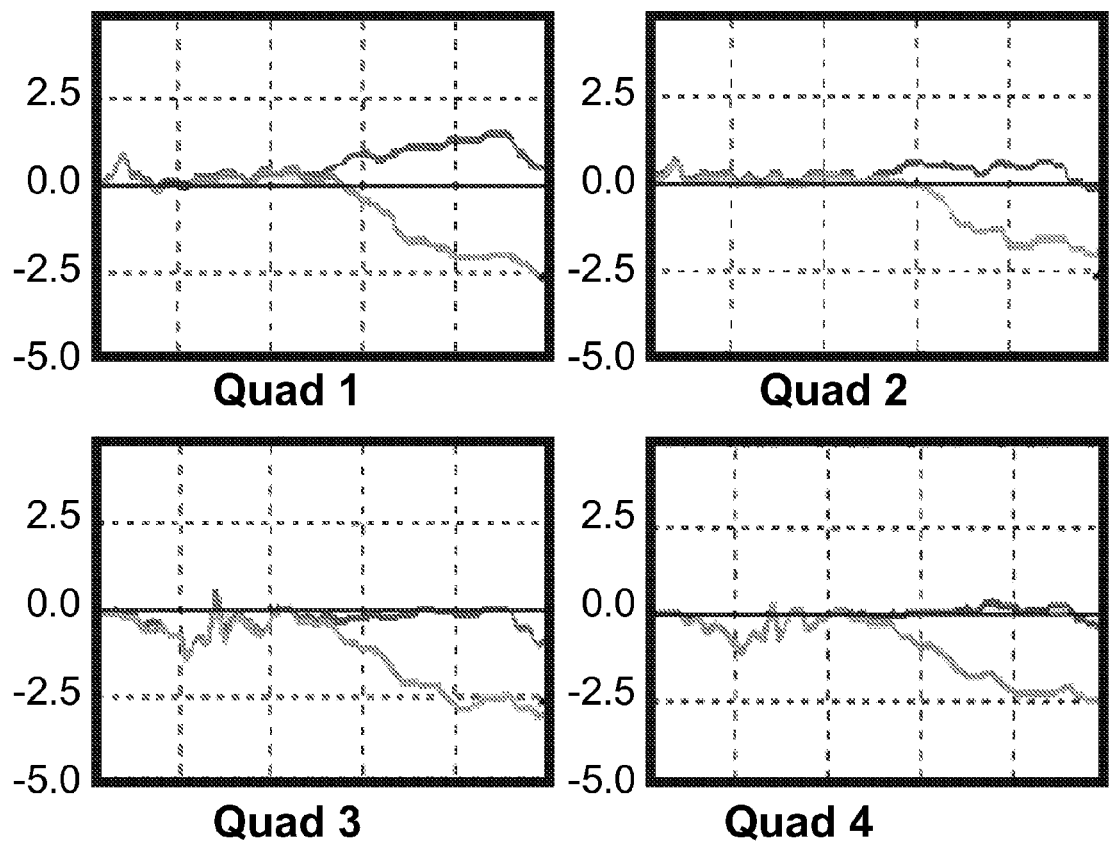
FIG. 15 illustrates the regional strain profiles within the phantom experiment described in the fourth example below.

As described above, zHARP images and automatically tracks the 3-D myocardial displacement of points in an image plane. ZHARP surpasses SF-CSPAMM, which only acquires the projection of a slice and implies that only in-plane x- and y-displacements can be obtained. An R-wave triggered tagged cardiac slice starts as a flat plane, undergoes in-plane and through-plane displacements and becomes a 3-D surface. As shown in FIG. 13, a through-plane rotation will be interpreted as in-plane compression when only x- and y-displacements are observed. With acquisition of the 3-D displacement components, this misinterpretation of rotation is removed and a true planar strain map is obtained by using a 3×3 displacement gradient tensor instead of a 2×2 tensor. Given a slice acquired through an object such as the myocardium, the strain tensor at a material point is defined by:

$$e = \frac{1}{2}[\nabla_x u + (\nabla_x u)^T] + \frac{1}{2}[(\nabla_x u)^T \times (\nabla_x u)] \text{ where} \quad (19)$$

$$\underline{u}(\underline{x}) = \underline{u}(x, y, z) = \begin{bmatrix} u_x \\ u_y \\ u_z \end{bmatrix} \text{ and } \nabla_{\underline{x}} \underline{u} = \begin{pmatrix} \frac{\partial u_x}{\partial x} & \frac{\partial u_x}{\partial y} & \frac{\partial u_x}{\partial z} \\ \frac{\partial u_y}{\partial x} & \frac{\partial u_y}{\partial y} & \frac{\partial u_y}{\partial z} \\ \frac{\partial u_z}{\partial x} & \frac{\partial u_z}{\partial y} & \frac{\partial u_z}{\partial z} \end{pmatrix}.$$

Compared to SF-CSPAMM, zHARP acquires $u_z$ in addition to $u_x$ and $u_y$, wherein the component $u_z$ is used to remove the false apparent strain due to through-plane rotation. With zHARP, this is done by adding $u_z$ into the computation of the displacement gradient as follows:

$$\nabla_{\underline{x}} \underline{u} = \begin{pmatrix} \frac{\partial u_x}{\partial x} & \frac{\partial u_x}{\partial y} & 0 \\ \frac{\partial u_y}{\partial x} & \frac{\partial u_y}{\partial y} & 0 \\ \frac{\partial u_z}{\partial x} & \frac{\partial u_z}{\partial y} & 0 \end{pmatrix}, \quad (20)$$

in contrast to using $$\nabla_{\underline{x}} \underline{u} = \begin{pmatrix} \frac{\partial u_x}{\partial x} & \frac{\partial u_x}{\partial y} \\ \frac{\partial u_y}{\partial x} & \frac{\partial u_y}{\partial y} \end{pmatrix}$$

with SF-SPAMM, wherein no $u_z$ is acquired.

We claim:

1. An apparatus for measuring three-dimensional motion of an object by magnetic resonance imaging from one acquired image orientation, comprising:
    a magnetic resonance scanner, wherein the magnetic resonance scanner is configured to:
        apply a magnetic resonance imaging pulse sequence to spatially modulate a region of interest of said object without the use of out-of-plane tags, the pulse sequence comprising a slice-following CSPAMM (complementary spatial modulation of magnetization) pulse sequence for encoding in-plane positions with added z-phase encode for encoding through-plane positions of points within the region of interest;
        acquire a set of one or more vertically tagged images and a set of one or more horizontally tagged images of said spatially modulated object, wherein the acquired sets of vertically and horizontally tagged images comprise both in-plane and through-plane encodings;
        extract a set of displacement-encoding phase maps from the acquired sets of vertically and horizontally tagged images; and
        determine in-plane and through-plane motions of said spatially modulated object based on the displacement-encoding phase maps, thereby generating a three-dimensional motion map of the points within the region of interest of said object.

2. The apparatus of claim 1, wherein the pulse sequence comprises a vertical tagging sequence having a first z-encoding gradient and a horizontal tagging sequence having a second z-encoding gradient of equal magnitude but opposite polarity, thereby adding through-plane encoding from which through-plane motion can be computed from the acquired images.

3. The apparatus of claim 2, the determining including computing a first two harmonic phase images for a vertically tagged image and a second two harmonic phase images for a horizontally tagged image.

4. The apparatus of claim 3, the determining further including solving a system of linear equations at a set of image coordinates for phase images indicating in-plane and through-plane motion, the system of linear equations formed by the four harmonic phase images computed for the vertically and horizontally tagged images.

5. The apparatus of claim 4, the determining further including applying harmonic phase (HARP) processing to compute in-plane motion of said spatially modulated object.

6. The apparatus of claim 5, the determining further including iterative application of a wrapping operator to compute through-plane motion of said spatially modulated object.

7. The apparatus of claim 1, wherein the magnetic resonance scanner is configured to obtain a real-time image of cardiac motion.

8. The apparatus of claim 1, wherein the magnetic resonance scanner is configured to obtain a real-time image of myocardial strain.

9. The apparatus of claim 1, wherein the magnetic resonance scanner is configured to obtain a dense three-dimensional motion map of points in a plane for computing myocardial surface strain.

10. The apparatus of claim 1, wherein the magnetic resonance scanner is configured to use a plurality of image planes to track a set of points within the myocardium for computing a three-dimensional measure of a regional function and global function.

11. The apparatus of claim 10, wherein the regional function comprises radial, circumferential, or longitudinal strain, principal strains, or the direction of maximal thickening.

12. The apparatus of claim 10, wherein global function comprises longitudinal shortening, rotation, or torsion.

13. The apparatus of claim 1, wherein the magnetic resonance scanner is further configured to:
   use a 3×3 displacement gradient tensor to remove an apparent false strain due to through-plane rotation; and
   compute a planar strain within the imaged slice;
   thereby differentiating between in-plane strain and three-dimensional rotation.

14. An apparatus for measuring three-dimensional motion of an object by magnetic resonance imaging from one acquired image orientation, comprising:

a magnetic resonance scanner, wherein the magnetic resonance scanner is configured to:
   apply a magnetic resonance imaging pulse sequence to spatially modulate a region of interest of said object without the use of out-of-plane tags, the pulse sequence comprising a slice-following CSPAMM (complementary spatial modulation of magnetization) pulse sequence for encoding in-plane position with added z-phase encode for encoding through-plane positions of points within the region of interest;
   acquire a set of one or more of grid tagged images of said spatially modulated object, wherein the acquired set of grid tagged images comprise both in-plane and through-plane encodings;
   extract a set of displacement-encoding phase maps from the acquired set of grid tagged images; and
   determine in-plane and through-plane motions of said spatially modulated object based on the displacement-encoding phase maps, thereby generating a three-dimensional motion map of the points within the region of interest of said object.

* * * * *